(12) United States Patent
Vaka et al.

(10) Patent No.: US 10,406,234 B2
(45) Date of Patent: Sep. 10, 2019

(54) METHOD OF MANUFACTURING FINE PARTICLES SUITABLE FOR ORALLY DISINTEGRATING PHARMACEUTICAL DOSAGE FORMS

(71) Applicant: Kashiv BioSciences, LLC, Bridgewater, NJ (US)

(72) Inventors: Siva Ram Kiran Vaka, Piscataway, NJ (US); Dipen Desai, Whippany, NJ (US); Wantanee Phuapradit, Montville, NJ (US); Navnit H. Shah, Clifton, NJ (US); Kanji Meghpara, Morris Plains, NJ (US)

(73) Assignee: Kashiv BioSciences, LLC, Bridgewater, NJ (US)

( * ) Notice: Subject to any disclaimer, the term of this patent is extended or adjusted under 35 U.S.C. 154(b) by 38 days.

(21) Appl. No.: 15/128,818

(22) PCT Filed: Mar. 24, 2015

(86) PCT No.: PCT/US2015/022289
§ 371 (c)(1),
(2) Date: Sep. 23, 2016

(87) PCT Pub. No.: WO2015/148538
PCT Pub. Date: Oct. 1, 2015

(65) Prior Publication Data
US 2017/0173157 A1   Jun. 22, 2017

Related U.S. Application Data

(60) Provisional application No. 61/969,347, filed on Mar. 24, 2014.

(51) Int. Cl.
*A61K 9/00* (2006.01)
*A61K 9/14* (2006.01)
(Continued)

(52) U.S. Cl.
CPC ............ *A61K 47/32* (2013.01); *A61K 9/0056* (2013.01); *A61K 9/146* (2013.01); *A61K 9/20* (2013.01);
(Continued)

(58) Field of Classification Search
None
See application file for complete search history.

(56) References Cited

U.S. PATENT DOCUMENTS 5,837,284 A * 11/1998 Mehta ................. A61K 9/1676
424/459
2004/0265370 A1   12/2004 Odidi et al.
2010/0047340 A1    2/2010 McGinity et al.

FOREIGN PATENT DOCUMENTS

WO       0235991         5/2002
WO       2004100883     11/2004
WO       2012101653 A2   8/2012

OTHER PUBLICATIONS

International Search Report for Application No. PCT/US2015/022289 dated Jun. 30, 2015.

* cited by examiner

*Primary Examiner* — Sreenivasan Padmanabhan
*Assistant Examiner* — Jody L Karol
(74) *Attorney, Agent, or Firm* — Lerner, David, Littenberg, Krumholz & Mentlik, LLP

(57) ABSTRACT

Disclosed are methods of making oral pharmaceutical compositions that contain substantially crush resistant drug containing microparticles. The microparticles may contain an active pharmaceutical agent, a polymer and a plasticizer. The microparticles may be un-coated (so as to impart an immediate release profile) or coated so as to impart an extended release (ER), delayed release (DR) or delayed extended release (DER) profile. One or more of the popu-
(Continued)

Schematic formulation design of the taste masking coated fine particles suitable for ODTs prepared by disclosed process compared to conventional process lations of microparticles may be coated with a taste masking composition. The methods may produce oral compositions such as orally disintegrating tablets that contain one or more these types of microparticles in order to further customize the release profile. Also disclosed are the oral compositions, per se, and methods of using same for their intended purposes.

17 Claims, 4 Drawing Sheets

(51) Int. Cl.
*A61K 9/20* (2006.01)
*A61K 9/28* (2006.01)
*A61K 9/50* (2006.01)
*A61K 47/32* (2006.01)
*A61K 47/38* (2006.01)

(52) U.S. Cl.
CPC ............ *A61K 9/2081* (2013.01); *A61K 9/28* (2013.01); *A61K 9/2893* (2013.01); *A61K 9/5026* (2013.01); *A61K 9/5042* (2013.01); *A61K 9/5073* (2013.01); *A61K 47/38* (2013.01)

Figure 1: Schematic formulation design of the taste masking coated fine particles suitable for ODTs prepared by disclosed process compared to conventional process
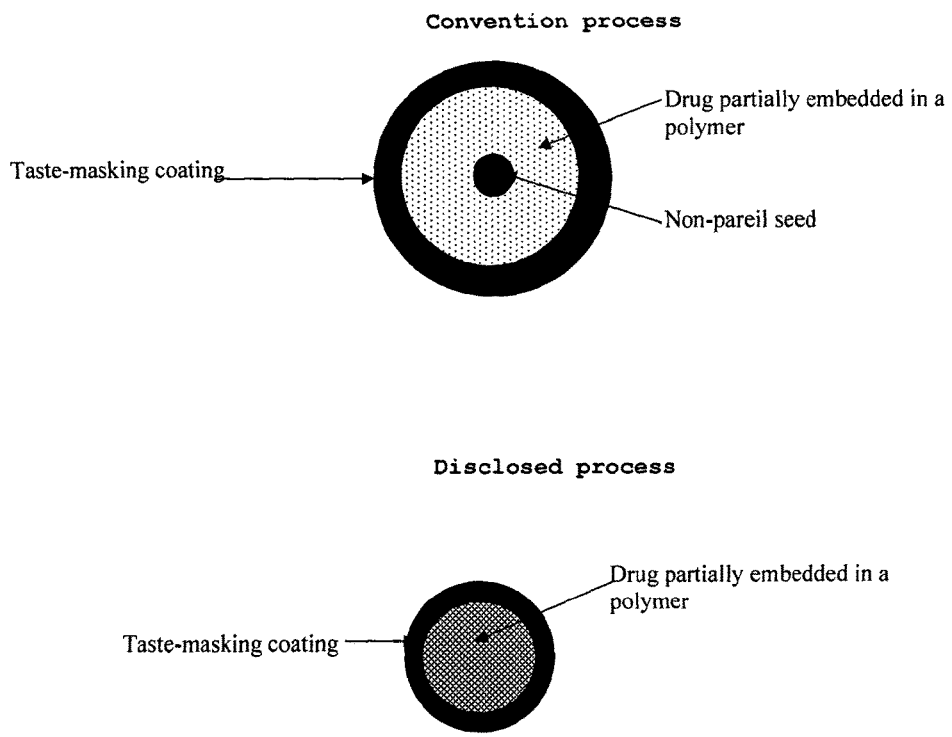

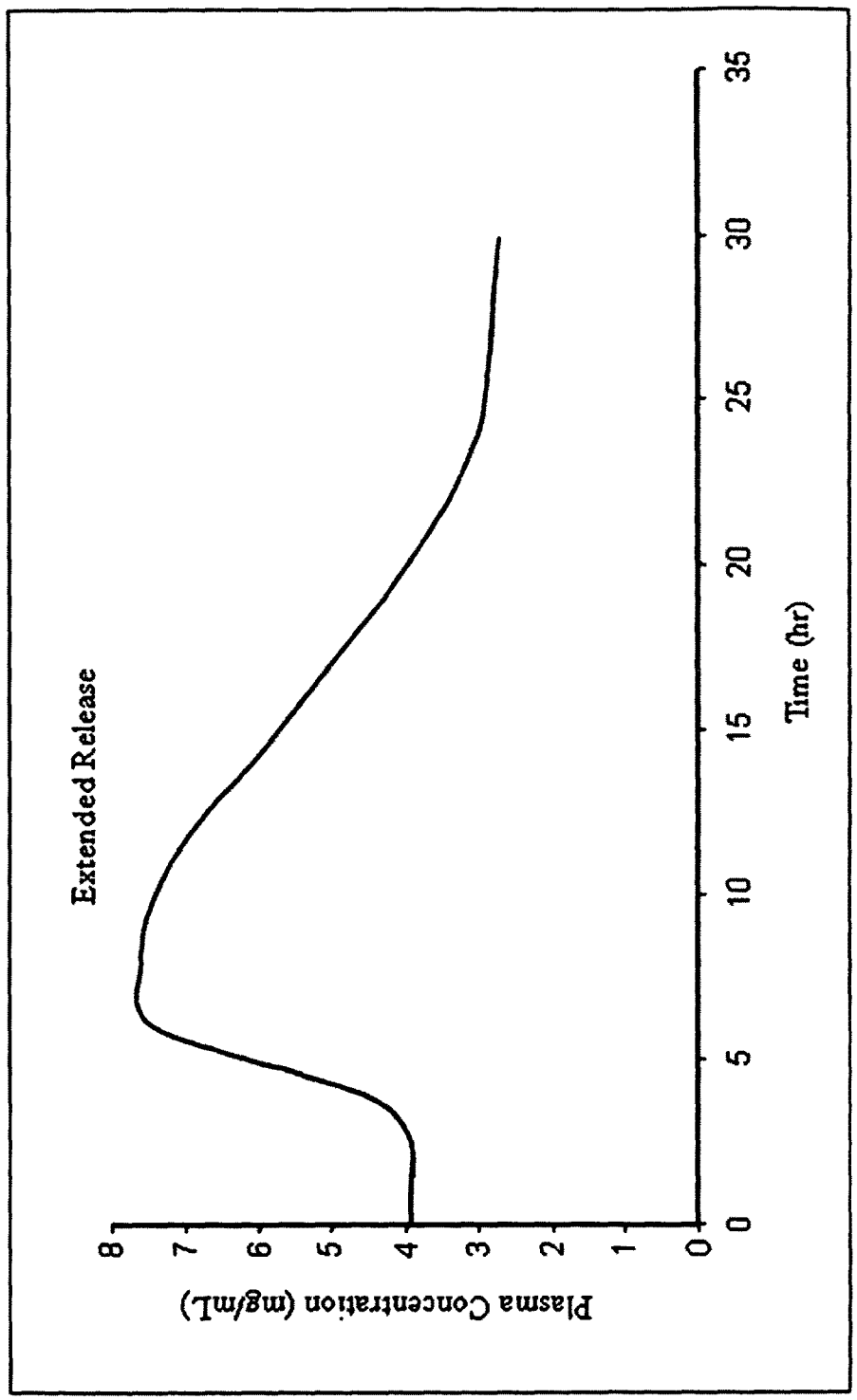
Figure 2: PK profile of novel extended release ODT

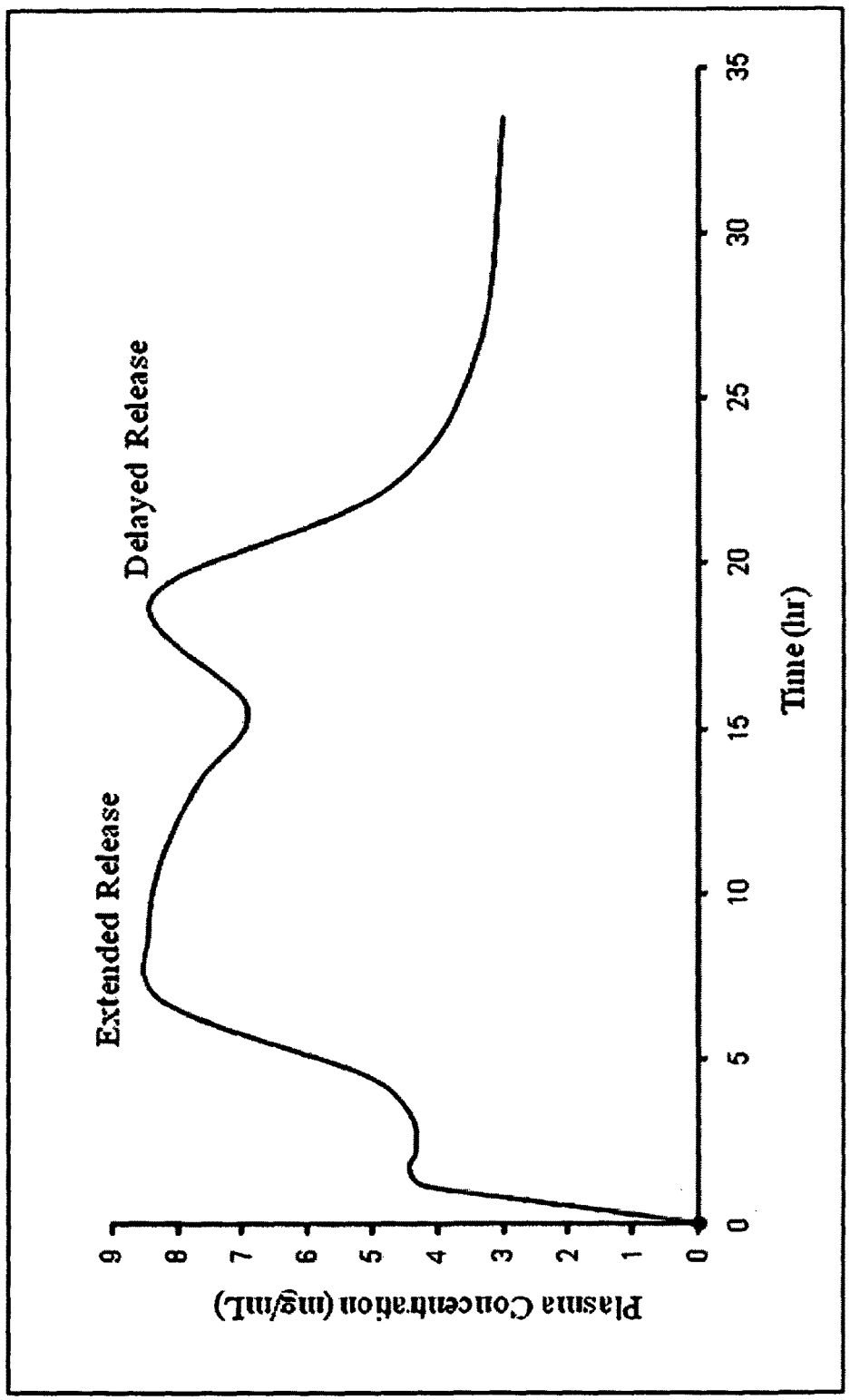
Figure 3: PK profile of novel modified release type I (extended release, followed by delayed release) ODT

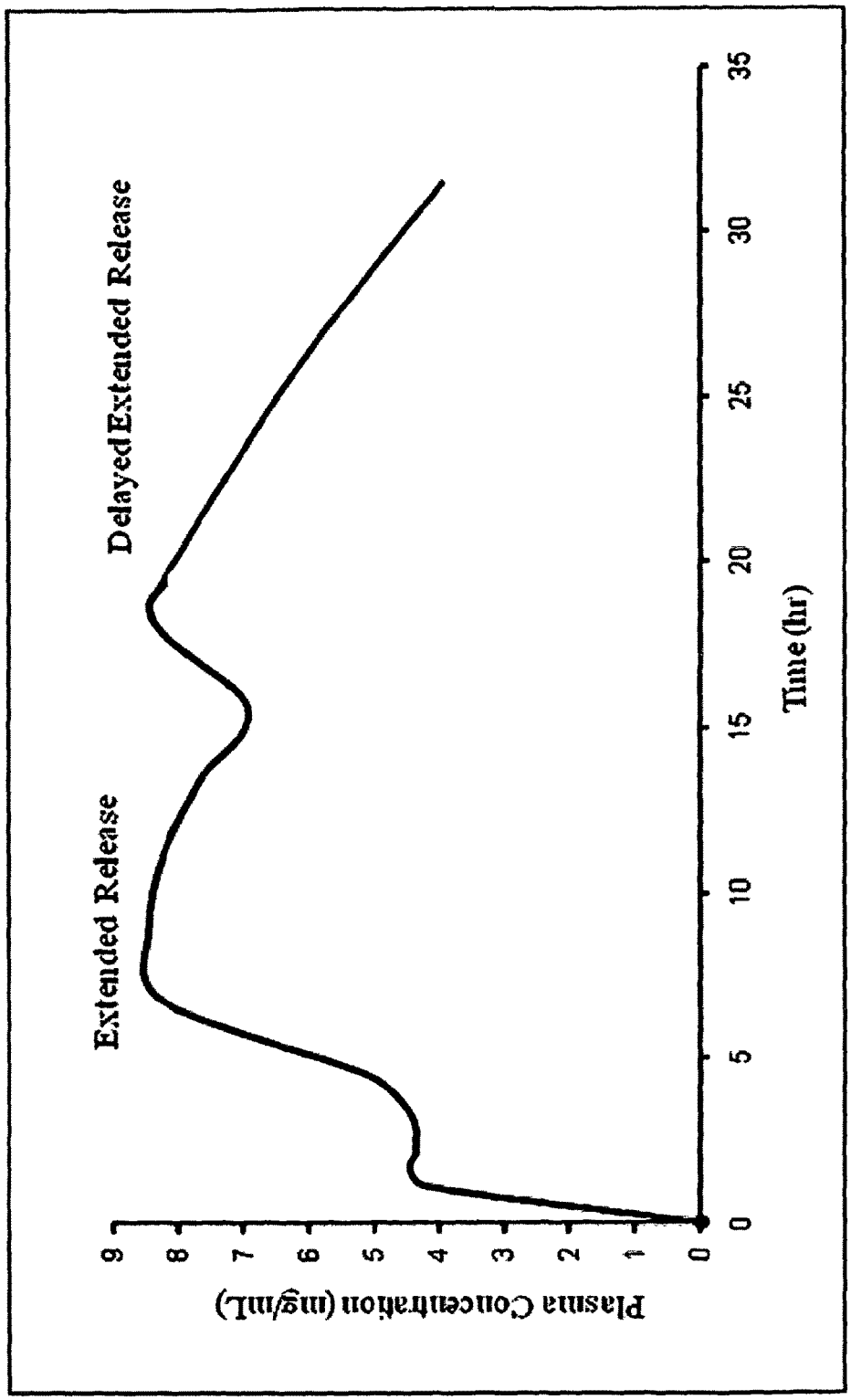
Figure 4: PK profile of novel modified release type II (extended release, followed by delayed extended release) ODT

METHOD OF MANUFACTURING FINE PARTICLES SUITABLE FOR ORALLY DISINTEGRATING PHARMACEUTICAL DOSAGE FORMS

CROSS-REFERENCE TO RELATED PATENT APPLICATION

The present application is a national phase entry under 35 U.S.C. § 371 of International Application No. PCT/US2015/022289 filed Mar. 24, 2015, published in English, which claims the benefit of the filing date of U.S. Provisional Application No. 61/969,347, filed Mar. 24, 2014, entitled "Orally Disintegrating Tablet Containing Taste Masking And Modified Release Coated Microparticles," the disclosures of which are hereby incorporated herein by reference.

BACKGROUND OF THE INVENTION

This disclosure relates to the field of orally disintegrating tablet containing microparticles with flexible release patterns and taste masking.

Multiparticulates are well known pharmaceutical dosage forms that can be utilized for a wide range of applications. When taken orally, multiparticulates generally disperse freely in the gastrointestinal (GI) tract, maximize absorption, and minimize side effects. See, for example, Multiparticulate Oral Drug Delivery (Marcel Dekker, 1994), and Pharmaceutical Pelletization Technology (Marcel Dekker, 1989).

Oral multiparticulate technology, in the form of beads, mini-tablets and microspheres with coated and/or matrix architecture, offers a wide range of drug release profile flexibility for single or multiple drug combinations. They can be formulated as modified-release (e.g., extended, delayed, pulsed), immediate-release, bioavailability-enhanced, or taste-masked dosage forms.

Extended release (ER) formulations provide several advantages, including, but not limited to, increased patient compliance, reduced dose frequency, and reduced side-effect profile. However, the potential therapeutic advantages of once daily extended release dosage forms with extended duration of release may be compromised by poor or unpredictable drug absorption from the colon. The rate and extent of absorption may be influence by the colon's physiological factors, such as less volume, highly viscous fluid, which thereby diminishes drug absorption. Multiparticulates provide predictable and consistent gastrointestinal transit and lower chances of undesirable events (e.g., dose dumping, colonic streaming) associated with single-unit dosage forms such as tablets. These multiparticulates can be dosed within capsules, tablets (microspheres, coated beads) or sachets. One application for multiparticulates is for delivery of drugs for which rapid delivery of the drug is desired for rapid onset of action. Such formulations must rapidly release the drug to the GI tract. For example, multiparticulates may be incorporated into orally disintegrating tablets (ODTs) that rapidly release the drug when the dosage form is placed into the mouth.

In such formulations, when the drug has an unpleasant taste it is often desirable to delay the release of the drug until the multiparticulate has exited the mouth to improve patient compliance. In order to provide taste masking, the materials used to form the multiparticulates must be capable of satisfying two competing constraints. On the one hand, the materials need to be sufficiently robust so as to remain intact and provide taste masking in the mouth. On the other hand, the materials used to provide taste masking should be capable of quickly releasing the drug once the multiparticulate has exited the mouth. If the materials that provide taste masking are too robust, then the materials may undesirably inhibit or slow the release of the drug in the GI tract. In addition, taste masked multiparticulates are fine enough to prevent grittiness in the mouth.

However, it is known to be difficult to coat fine particles (d50 less than 200 microns) uniformly for taste masking, extended release or modified release applications. One problem is due to attrition of the particles during fluid bed coating. Another problem is that granules and multiparticulates can often present a gritty sensation in the patient's mouth. A further problem is that due to electrostatic charge interactions during manufacturing, microparticles are prone to agglomeration prior to coating. It is desired that a dosage form provide a pleasing feel in the mouth.

There is therefore a need to develop fine particle suitable for modified release and/or taste masked orally disintegrating dosage forms that improve patient compliance, target drug release at specific site of absorption, maximize colonic absorption, reduce peak-to-trough variations, and maintain plasma levels within therapeutic ranges.

BRIEF SUMMARY OF THE INVENTION

A first aspect of the present invention pertains to a method for making a pharmaceutical composition containing substantially crush-resistant drug-containing microparticles that are suitable for making ODTs. In some embodiments, the microparticles are formed by subjecting an active pharmaceutical ingredient, a polymer, and a plasticizer to hot melt extrusion, whereby the molten mass that is formed is extruded, and then milling the extrudate to produce fine particles with a narrow particle size distribution, e.g., mean particle size ranging from about 50 microns to about 250 microns. The extrudate may be cooled before, during or both before and during milling. The microparticles, which may exhibit an immediate-release (IR) profile, may then be coated to impart taste-masking and/or another desired drug-release profile. Also, one or more separate populations of the IR microparticles may be produced, which also may be coated to impart either or both of these properties. Thus, in some embodiments, the release profile of the microparticle formulation is customized, and includes selected combinations of amounts of the immediate-release (IR), extended release (ER), delayed-release (DR) microparticles, and/or delayed extended release (DER). The one or more populations of microparticles may then be formulated (e.g., compressed) into the desired dosage form which in some embodiments, is an orally disintegrating tablet.

Another aspect of the present invention is directed to orally disintegrable dosage forms containing substantially crush-resistant immediate-release microparticles, that may be prepared using the inventive methods. In one embodiment, the oral pharmaceutical composition contains a first population of immediate-release microparticles containing an active pharmaceutical agent, a first plasticizer and a first polymer, wherein the total amount of the active pharmaceutical agent in the composition is therapeutically effective, and wherein the first plasticizer is present in the microparticles in amounts effective to render the microparticles substantially crush resistant. The first population of microparticles may be coated with a taste-masking composition.

In some embodiments, the first population of microparticles is coated with an extended-release coating comprising a second polymer and a second plasticizer, (and in some other embodiments a pore forming material), wherein the first and second plasticizer may be the same or different, and wherein the first and second polymer may be the same or different, and further wherein the thus-coated microparticles are a second population of extended release, substantially crush resistant microparticles. In some embodiments, the second polymer also acts as a pore-forming material; in some other embodiments, the pore-forming material is non-polymeric.

In some embodiments, the first population of microparticles is coated with a delayed-release coating comprising a third polymer and a third plasticizer, wherein the first, second and third plasticizers may be the same or different, and wherein the first, second and third polymers may be the same or different, wherein the thus-coated microparticles are a third population of delayed release, substantially crush resistant microparticles.

In some embodiments, the first population of microparticles is coated with i) an extended-release coating comprising a second polymer and a second plasticizer, and ii) a delayed-release coating comprising a third polymer and a third plasticizer, wherein the first, second and third plasticizers may be the same or different, and wherein the first, second and third polymers may be the same or different, wherein the thus-coated microparticles are a fourth population of delayed-extended release, substantially crush resistant microparticles. Thus, in some embodiments, the composition may include the first, second, third or fourth population of microparticles.

In some embodiments, the oral pharmaceutical composition contains a mixture of two or more of the first, second, third and fourth populations of microparticles, and thus provides a customized release profile. Thus, in some embodiments, the composition contains an amount of the first population of immediate release, substantially crush-resistant microparticles and an amount of the second population of extended release, substantially crush resistant microparticles. In other embodiments, the composition contains an amount of the first population of immediate release, substantially crush-resistant microparticles and an amount of the third population of delayed release, substantially crush resistant microparticles. In other embodiments, the composition contains an amount of the first population of immediate release, substantially crush-resistant microparticles and an amount of the fourth population of delayed extended release, substantially crush resistant microparticles. In other embodiments, the composition contains an amount of the first population of immediate release, substantially crush-resistant microparticles and an amount of each of the second and third populations of substantially crush resistant microparticles. In other embodiments, the composition contains an amount of the first population of immediate release, substantially crush-resistant microparticles and an amount of each of the second and fourth populations of substantially crush resistant microparticles. In other embodiments, the composition contains an amount of the first population of immediate release, substantially crush-resistant microparticles and an amount of each of the third and fourth populations of substantially crush resistant microparticles.

In other embodiments, the composition contains an amount of the second population of extended release, substantially crush resistant microparticles and an amount of the third population of delayed release, substantially crush resistant microparticles. In yet other embodiments, the composition contains an amount of the second population of extended release, substantially crush resistant microparticles and an amount of the fourth population of delayed-extended release, substantially crush resistant microparticles. In yet other embodiments, the composition contains an amount of the third population of delayed release, substantially crush resistant microparticles and an amount of the fourth population of delayed-extended release, substantially crush resistant microparticles.

BRIEF DESCRIPTION OF THE DRAWINGS

FIG. 1 is a schematic formulation design of the taste masking coated fine particles suitable for ODTs prepared by disclosed process compared to a conventional process. The microparticles prepared in accordance with the present invention are crush resistant and are fine enough to avoid grittiness in the mouth.

FIG. 2 is a graph showing a prophetic pharmacokinetic (PK) profile of an embodiment of an extended-release orally disintegrating tablet (ODT) of the present invention.

FIG. 3 is a graph showing a prophetic PK profile of an embodiment of a modified release type I (extended release, followed by delayed-release) ODT of the present invention.

FIG. 4 is a graph showing a prophetic PK profile of an embodiment of a modified release type II (extended release, followed by delayed extended release) ODT of the present invention.

DETAILED DESCRIPTION

Definitions

"Drug", "active agent", "active pharmaceutical ingredient (API)," and "pharmaceutically active agent" are used interchangeably herein to refer to a chemical compound that induces a desired pharmacological and/or physiological effect. The terms also encompass pharmaceutically acceptable derivatives of those active agents specifically mentioned herein, including salts, solvates, hydrates, complexes with one or more molecules, pro-drugs, active metabolites, lipophilic derivatives, analogs, and the like.

As used herein, the term "solid dosage form" generally refers to a pharmaceutical composition, which when used in an oral mode of administration includes capsules, tablets, pills, powders and granules. In such solid dosage forms, the active compound is mixed with at least one inert, pharmaceutically acceptable excipient or carrier.

The terms "melt" and "melting" should be interpreted broadly. For our purposes, these terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties or may form solid dispersion of the drug and polymer.

The terms "microparticle" and "fine particle" as used herein refer to a discrete, particle unit containing at least one active pharmaceutical ingredient and at least one excipient, and which has a diameter of less than 1000 microns. A "population of microparticles or fine particles as used herein refers to a multiplicity of discrete particles having a d50 within certain specified amounts, e.g., about 50 to about 250 microns.

The term "narrow particle size distribution" refers to a sample that exhibits a Gaussian distribution with a standard deviation (σ) that is less than 1 with particle size distribution preferably in the range of 25-500 microns; more preferably in the range of 50-400 microns; most preferably in the range of 75-300 microns.

The term "orally disintegrating tablet (ODT)" refers to solid dosage form designed to dissolve in the oral cavity.

The term "substantially crush-resistant" refers to materials that resist breaking or attrition into smaller pieces during functional coating process or upon compaction into tablets.

The term "highly plasticized" refers to materials that are characterized by plastic deformation when subject to compaction. This term is used interchangeably herein with "substantially crush resistant."

The term "taste masking" refers to a perceived reduction of an unpleasant taste that would otherwise exist.

The term "immediate release" as used herein means that the bulk of the drug is released from the dosage form in which it is administered in the stomach. By "bulk," it is meant that at least about 50% of the drug should be released within 60 minutes. In many cases, that release will be as quickly as practicable, i.e., dissolution will be as close to that resulting from administering an equal amount of fine loose powder."

The term "extended release" as used herein means that the composition is formulated to make the drug available over a greater period of time after ingestion thereby allowing a reduction in dosing frequency, as compared to a drug presented as a conventional dosage form (e.g., as a solution or an immediate release dosage form).

The term "delayed-release" refers to pharmaceutical dosage forms that are designed to pass through the stomach unaltered and later release an active pharmaceutical ingredient within the intestinal tract.

The term "delayed extended-release" refers to pharmaceutical dosage forms that are designed to pass through the stomach unaltered and later release an active pharmaceutical ingredient within lower part of intestinal tract at a predetermined rate and duration.

The term "modified-release" more generally refers to pharmaceutical dosage forms that provide extended release, and/or delayed release of an active pharmaceutical ingredient.

Immediate Release (IR) Microparticles

The present invention entails preparation and use of substantially crush-resistant immediate-release microparticles. They may contain an active pharmaceutical ingredient, a plasticizer and a polymer. The API and plasticizer may be embedded in a matrix of the polymer.

Representative examples of APIs that may be suitable for use in the present invention include members of the therapeutic categories including: analgesics, anti-inflammatory agents, anthelmintics, anti-arrhythmic agents, anti-bacterial agents, anti-viral agents, anticoagulants, anti-depressants, anti-diabetic agents, anti-epileptic agents, anti-fungal agents, anti-gout agents, anti-hypertensive agents, anti-malarial agents, anti-migraine agents, anti-muscarinic agents, anti-neoplastic agents, erectile dysfunction improving agents, immunosuppressants, anti-protozoa agents, anti-thyroid agents, anti-anxiolytic agents, sedatives, hypnotics, neuroleptics, β-blockers, cardiac inotropic agents, corticosteroids, diuretics, anti-Parkinsonian agents, gastrointestinal agents, histamine receptor antagonists, keratolytics, lipid regulating agents, anti-angina agents, cox-2 inhibitors, leucotriene inhibitors, macrolides, muscle relaxants, nutritional agents, opioid analgesics, protease inhibitors, sex hormones, stimulants, anti-osteoporosis agents, anti-obesity agents, cognition enhancers, anti-urinary incontinence agents, nutritional oils, anti-benign prostate hypertrophy agents, essential fatty acids, non-essential fatty acids, and any combinations of two or more thereof.

In some embodiments, the APIs are selected from those commonly prescribed for ADHD. Representative examples of such APIs include methylphenidate, dexmethylphenidate, dextroamphetamin, and amphetamine.

In some embodiments, the APIs are selected from those commonly prescribed for HIV. In some embodiments, the API is a nucleoside reverse transcriptase inhibitor (NRTI). In some embodiments, the API is a non-nucleoside reverse transcriptase inhibitor (NNRTI). In some embodiments, the API is a protease inhibitor (PI). In some embodiments, the API is a fusion inhibitor. In some embodiments, the API is an integrase inhibitor. In some embodiments, the API is a CCR5 antagonist. In further embodiments, the active pharmaceutical ingredient is selected from efavirenz, emtricitabine, tenofovir, ritonavir, raltegravir, atazanavir, emtricitabine, rilpivirine, lopinavir, fosamprenavir, abacavir, darunavir, indinavir, nelfinavir, saqyubavurm tipranavir, indinavir, lamivudine, zidovudine, etravirine, nevirapine, stavudine, enfuvirtide, emtricitabine, didanosine, delavirdine, rilpivirine, raltegravir, maraciroc, and pharmaceutically acceptable salts thereof, and mixtures thereof.

The pharmaceutically active agent is present in the formulation in an amount effective for the intended therapeutic purpose. These amounts are well known in the art. Indeed, all of the active agents embraced by the present invention are known per se, as are the doses at which they can be given safely and effectively for the intended therapeutic purpose.

Representative examples of polymers that may be suitable for use in preparing the IP microparticles of the present invention include pH-dependent polymers and pH-independent polymers. Types of polymers that fall into either of these categories include (meth)acrylic polymers and (meth)acrylic copolymers (e.g., copolymers of alkyl (meth)acrylates and copolymers of alkylamino(meth)acrylates), quaternary ammonium (meth)acrylic polymers, and cellulose derivatives. Representative examples of pH-dependent polymers and nonionic pH-independent polymers are listed in Table 1.

TABLE 1

Exemplary Polymers to Form IR Microparticles

| Polymers | Trade Name/Supplier |
|---|---|
| Cationic copolymer based on dimethylaminoethyl methacrylate, butyl methacrylate, and methyl methacrylate (Cationic pH-dependent polymer) | EUDRAGIT ® E PO/Evonik (Chemical/IUPAC name: Poly(butyl methacrylate-co-(2-dimethylaminoethyl) methacrylate-co-methyl methacrylate) 1:2:1) |

TABLE 1-continued

Exemplary Polymers to Form IR Microparticles

| Polymers | Trade Name/Supplier |
|---|---|
| Copolymer of ethyl acrylate, methyl methacrylate and a low content of methacrylic acid ester with quaternary ammonium groups (Ammonium Methacrylate Copolymer, Type A, NF) (Non-ionic pH-independent polymer) | EUDRAGIT ® RL 100, RS100/Evonik (Chemical/IUPAC name for RL 100: Poly(ethyl acrylate-co-methyl methacrylate-co-trimethylammonioethyl methacrylate chloride) 1:2:0.2) |
| Copolymer of ethyl acrylate, methyl methacrylate and a low content of methacrylic acid ester with quaternary ammonium groups (Ammonium Methacrylate Copolymer, Type B, NF) (Non-ionic pH-independent polymer) | EUDRAGIT ® RS100/Evonik (Chemical/IUPAC name: Poly(ethyl acrylate-co-methyl methacrylate-co-trimethylammonioethyl methacrylate chloride) 1:2:0.1) |
| Hydroxypropylcellulose (Non-ionic pH-independent polymer) | Klucel ™ E, L, J, G, M and H grades/Ashland |
| Hydroxypropyl methylcellulose (Non-ionic pH-independent polymer) | METHOCEL ™ E, F, J, and K/Dow Chemicals |
| Hydroxyethylcellulose (Non-ionic pH-independent polymer) | NATRASOL ™ L, G, M and H grades/Ashland |
| Ethylcellulose (Non-ionic pH-independent polymer) | ETHOCEL ™ 7FP, 10FP, 45FP and 100 FP/Dow Chemicals N7, N 10, N14, N22, N50 and N100 grades/Ashland |
| Cellulose Acetate Butyrate (Non-ionic pH-independent polymer) | CAB-381-0.5/Eastman |
| Cellulose Acetate (Non-ionic pH-independent polymer) | CA-398-3, CA-398-6, CA-398-10, CA-398-30/Eastman |

Exemplary pH-dependent polymers include cationic pH-dependent release polymers that are soluble in gastric fluid, but swell and become permeable at pHs above 5.0. In some embodiments, the cationic pH-dependent polymer includes EUDRAGIT® E PO has a molecular weight about 47,000 and a glass transition temperature about 48° C. EUDRAGIT® E PO is soluble in gastric fluid up to pH 5.0; however, it is not soluble above pH 5.0, but is swellable and permeable above pH 5.0. As a result, EUDRAGIT® E PO will suddenly slow down release of drug into the intestinal fluid. Due to the uniqueness of its chemical properties, EUDRAGIT® E may act as an absorption retardant polymer when ingested in overdose quantities.

Yet other polymers that may be present in the IR microparticles are hydrophilic polyethylene oxide polymers. These polymers form viscous gels upon contact with aqueous media. Examples of useful polyethylene oxide polymers that are sold as POLYOX® by The Dow Chemical Co. are listed in Table 2 below (wherein the superscripts a, b and c refer to 5%, 2% and 1% solutions, respectively, measured at 25° C. using a Brookfield viscometer in accordance with the manufacturer's instructions).

TABLE 2

Representative Polyethylene oxide Polymers

| Trade Name | INCI Name | Approx. Molecular Weight | Viscosity (mPa · s) |
|---|---|---|---|
| POLYOX ® WSR-205 | PEG-14M | 600,000 | about 4500-about 8800[a] |
| POLYOX ® WSR-301 | PEG-90M | 4,000,000 | about 1650-about 5500[c] |
| POLYOX ® WSR N-10 | PEG-2M | 100,000 | about 12-about 50[a] |
| POLYOX ® WSR N-80 | PEG-5M | 200,000 | about 65-about 115[a] |
| POLYOX ® WSR N-750 | PEG-7M | 300,000 | about 600-about 1,000[a] |
| POLYOX ® WSR N-3000 | PEG-14M | 400,000 | about 2250-about 4500[a] |
| POLYOX ® WSR N-12K | PEG-23M | 1,000,000 | about 400-about 800[b] |
| POLYOX ® WSR N-60K | PEG-45M | 2,000,000 | about 200-about 400[b] |

Examples of other polymers that may be useful include pectin, polysaccharides such as pectin, crosslinked starches, and cellulose derivatives such as sodium carboxymethycellulose and hypromellose acetate succinate (HPMCAS) (e.g., HPMCAS-grade MF), silicone polymers, carbomers (such as Carbopol 934P NF, Carbopol 974P NF and Carbopol 971P NF, available from Noveon Pharmaceuticals), polycarbophil tragacanth, and gums such as xanthan gum.

The polymer is present in an amount that contributes or helps impart the property of substantial crush resistance. The polymer may be present in the IR microparticles in an amount that generally ranges from about 0.1 g/g (or 10% w/w to about 0.99 g/g (or 99% w/w), and in other embodiments, in a range of about 0.2 g/g (or 20% w/w) to about 0.8 g/g (or 80% w/w), and in some other embodiments, from about 0.3 g/g (30% w/w) to about 0.5 g/g (50% w/w) based on the total weight of the IR microparticles.

It is believed that the plasticizer functions to increase the elasticity of the polymer within microparticles, which therefore makes the IR microparticles highly plasticized and substantially crush-resistant. Representative examples of plasticizers that may be suitable for use in the IR microparticles include liquid esters, e.g., triethyl citrate, propylene glycol, polyethylene glycols, triacetin, diethylene glycol monoethyl ether, dibutyl sebacate, diethyl phthalate, fatty acids (e.g., stearic acid), fatty alcohols (e.g., cetyl alcohol) and glyceryl monostearates. In some embodiments, the dielectric constant values of the plasticizer are in a range of about 5 to about 60. In other embodiments, the dielectric constant values of the plasticizer are in a range of about 10 to about 40.

The plasticizer may be present in an amount that is sufficient to make the IR microparticles substantially crush-resistant, but does not negatively impact the dissolution of the API. The amount of the plasticizer improves the elongation percent of the extruded mass (e.g., by as much as 10%, 15%, 20%, 25% or more, compared to extrudates that do not contain a plasticizer), enabling the resultant microparticles withstand harsh processing conditions without breaking apart. The crush-resistance of the microparticles may be determined by a measurement of a breaking strength or resistance to breaking of the particulates using an Instron Tester or equivalent. One skilled in the art will be able to select an appropriate amount of plasticizer to use in preparing the IR microparticles. The plasticizer may be present in the IR microparticles in an amount that generally ranges from about 0.01 g/g (or 1% w/w) to about 0.4 g/g (or 40% w/w) based on the polymer weight, and in some embodiments, from about 0.02 g/g (or 2% w/w) to about 0.25 g/g (or 25% w/w), and in some other embodiments, from about 10% (w/w) to about 20% (w/w) of the weight of the polymer in the IR microparticles.

Manufacturing Process for Immediate-Release Microparticles

Producing the IR microparticles or fine particles of the present invention is advantageously achieved by a combination of hot melt extrusion followed by milling. Hot-melt extrusion equipment typically includes an extruder, auxiliary equipment for the extruder, downstream processing equipment, and other monitoring tools used for performance and product quality evaluation. The extruder is typically composed of a feeding hopper, barrels, single or twin screws, and the die and screw-driving unit. The auxiliary equipment for the extruder mainly consists of a heating/cooling device for the barrels, a conveyer belt to cool down the product and a solvent delivery pump. The monitoring devices on the equipment include temperature gauges, a screw-speed controller, an extrusion torque monitor and pressure gauges. Different sections of the barrel can be maintained at different temperatures.

In hot melt extrusion, the API, polymer, and the plasticizer may be introduced (e.g., in the form of a powdery mixture) into one or two rotating screws that convey the powder into a heated zone where shear forces are imparted into the mixture, compounding the materials until a molten mass is achieved. Extrudates can be produced from the molten mass by extruding through dies onto cooled rolls. Extruded strands are cut into desired length. Cutting is performed after cooling of the strand on conveyer belts. More generally, the extrudate can be cooled before, during or both before and during the milling.

Milling the extrudate to a smaller particle size eliminates the gritty texture of the microparticles thus providing acceptable mouthfeel. In some embodiments, grinding of the hot-melt extrudates yields IR microparticles with mean particle sizes from about 50 microns to 250 microns. In some embodiments, grinding of the hot-melt extrudates yields IR microparticles with a size distribution with mean particle sizes from about 50 microns to 150 microns (narrower range). In some embodiments, grinding of the hot-melt extrudates yields microparticles A with a size distribution with mean particle sizes of less than 150 microns.

Cryo-milling (which is advantageously employed when the polymer is thermoplastic) of the rubbery extrudates yields microparticles with a particle size distribution ranging from 25 microns to 500 microns and the mean particle size ranging from 50 microns to 250 microns.

The process disclosed herein is believed to circumvent the issue of solvent removal and secondary drying in that it is a process in which particle formation is carried out from a molten state rather than a solution state.

Extended-Release (ER) Microparticles

The highly plasticized, substantially crush-resistant extended-release microparticles contain the immediate-release microparticle described above, wherein the microparticles are coated with an extended-release coating composition containing an extended release polymer and a plasticizer. In some embodiments, the extended release coating composition also includes a pore-forming material.

Representative examples of polymers that may be suitable for use in the extended-release coating composition include polyvinyl acetate/polyvinylpyrrolidone (e.g., Kollicoat® SR), Cellulose Acetate, Cellulose Acetate Butyrate, Eudragit® RL 100, Eudragit® RS 100, Eudragit® NE-40D, Eudragit® NE-30D and ethylcellulose (e.g., Ethocel® 10 cps, 45 cps, 100 cps). EUDRAGIT® RS 100 and RL 100 are copolymers of ethyl acrylate, methyl methacrylate and a low content of methacrylic acid ester with quaternary ammonium groups, wherein the ammonium groups are present as salts and make the polymers permeable. The second polymer may be present in the extended release coating in an amount generally ranging from about 0.05 g/g (or 5% w/w to about 0.6 g/g (or 60% w/w) based on the coating weight gain on dried basis, and in other embodiments, from about 0.01 g/g (or 1% w/w) or about 0.1 g/g (or 10% w/w) to about 0.3 g/g (or 30% w/w) based on the coating weight gain on a dried basis.

It is believed that the plasticizer increases the elasticity of the polymer in the extended release coating, which therefore makes the extended release coating highly plasticized and substantially crush-resistant. Representative examples of plasticizers that may be suitable for use in the extended-release coating composition include liquid esters, e.g., triethyl citrate, propylene glycol, polyethylene glycols, triacetin, diethylene glycol monoethyl ether, dibutyl sebacate, diethyl phthalate, and combinations thereof. In some embodiments, the dielectric constant values of the plasticizer are in a range of about 5 to about 60. In other embodiments, the dielectric constant values of the second plasticizer are in a range of about 10 to about 40.

The plasticizer may be present in an amount that is sufficient to make the extended-release coating substantially crush-resistant, once applied to the microparticle. One skilled in the art will be able to select an appropriate amount of plasticizer to add to the composition. In general, the plasticizer may be present in an amount that ranges from about 0.02 g/g (or 2% w/w) to about 0.3 g/g (or 30% w/w) based on the weight of the extended release polymer, and in some embodiments, from about 0.05 g/g (or 5% w/w) to about 0.15 g/g (or 15% w/w) of based on the weight of extended release polymer. The plasticizer level may provide an adequate rubbery state with percent elongation at break in the range of about 100% to about 400% as determined by a texture analyzer using a casted free film strip.

The extended-release microparticle coating may contain a pore-forming material that alters the permeability of the extended-release coating. In some embodiments, the pore-forming material is a polymer, e.g., a pH-dependent polymer or a pH-independent polymer. Representative examples of suitable pH-dependent, pore-forming polymers include Eudragit L100-55, Hydroxypropyl Methylcellulose Phthalate, Hypromellose Acetate Succinate (e.g., AFFINISOL™, Shin-Etsu AQOAT®)). Representative examples of suitable pH-independent, pore-forming polymers include Hydroxylpropyl Methylcellulose (e.g., Methocel K3, E3, E5, E6, E15, Pharmacoat 603, Pharmacoat 606), Hydroxylpropyl Cellulose (e.g., Klucel EF, Klucel LF), Polyethylene Glycol 400, 1450, 3350, 6000, 8000 and 20,000.

In some embodiments, non-polymeric pore-forming materials may be present. Representative examples include lactose, sucrose, mannitol and propylene glycol.

The non-polymeric pore-forming material may be present in an amount that ranges from about 0.02 g/g (2% w/w) to about 0.4 g/g (40% w/w), and in some embodiments, from about 0.05 g/g (5% w/w) to about 0.2 g/g (20% w/w), based on the weight of the polymer in the ER coating composition.

Manufacturing Process for Extended-Release (ER) Microparticles

The extended-release coating may be prepared by dissolving the polymer and the second plasticizer in a solvent. In some embodiments, the solvent is aqueous. In other embodiments, the solvent is organic. In some embodiments, the solvent is an alcohol such as ethyl alcohol or isopropyl alcohol.

The extended-release coating may be applied to the immediate-release microparticles in a coating pan. In other embodiments, the controlled release coating is applied to IR microparticles using a Wuster column in a fluid bed dryer.

Delayed Release Microparticles

The substantially crush-resistant delayed-release microparticles contain the immediate-release microparticles described above, but which are coated with a delayed release coating containing a polymer and a plasticizer.

Representative examples of polymers that may be useful in the extended-release coatings include Eudragit® L100-55, Hydroxypropyl Methylcellulose Phthalate, Hypromellose Acetate Succinate (e.g., Shin-Etsu AQOAT), Cellulose Acetate Phthalate, Polyvinyl Acetate Phthalate, Eudragit® L100, and Eudragit® S100. The polymer may be present in the delayed-release coating in an amount that ranges from about 0.10 g/g (or 10% w/w to about 0.60 g/g (or 60% w/w) based on the coating weight gain on dried basis, and in other embodiments, from about 0.2 g/g (or 20% w/w) to about 0.4 g/g (or 40% w/w) based on the coating weight gain on a dried basis.

The polymer in the extended-release coating may the same or different from the polymers present in the immediate-release microparticles or in the coating of the delayed-release microparticles.

It is believed that the plasticizer functions to increase the elasticity of the polymer within the delayed release coating, which therefore makes the delayed release coating highly plasticized and substantially crush-resistant. Representative examples of plasticizers that may be useful in the extended-release coating composition include liquid esters, e.g., triethyl citrate, propylene glycol, polyethylene glycols, triacetin, diethylene glycol monoethyl ether, dibutyl sebacate, and diethyl phthalate. In some embodiments, the dielectric constant values of the third plasticizer are in a range of about 5 to about 60. In other embodiments, the dielectric constant values of the third plasticizer are in a range of about 10 to about 40.

The plasticizer may be present in an amount that is sufficient to make the delayed release coating substantially crush-resistant, once applied to a microparticle. One skilled in the art will be able to select an appropriate amount of plasticizer to add to the delayed-release coating composition. In general, the plasticizer may be present in the delayed release coating in an amount that ranges from about 0.02 g/g (or 2% w/w) to about 0.3 g/g (or 30% w/w), and in some embodiments, from about 0.05 g/g (or 5% w/w) to about 0.15 g/g (or 15% w/w) based on the weight of the polymer contained in the delayed-release coating composition. The plasticizer level provides an adequate rubbery state with percent elongation at break in the range of about 100% to about 400% as determined by a texture analyzer using a casted free film strip.

Manufacturing Process for Delayed-Release (DR) Microparticles

In some embodiments, the delayed-release coating may be prepared by dissolving the polymer and the plasticizer in a solvent. In some embodiments, the solvent is aqueous. In other embodiments, the solvent is organic. In some embodiments, the solvent is an alcohol. In further embodiments, the solvent contains water and an organic solvent such as isopropyl alcohol, ethanol, and acetone. In some embodiments, the ratio of organic solvent to water is in the range of about 90:10 to about 70:30.

In some embodiments, the delayed release coating is applied to the immediate-release microparticles in a coating pan. In other embodiments, the delayed release coating is applied to the immediate-release microparticles using a Wuster column in a fluid bed coater.

Delayed Extended-Release (DER) Microparticles

The substantially crush-resistant delayed extended-release microparticles include the extended-release microparticle described above, but which are further coated with a delayed release coating containing a polymer and a plasticizer, all as described above in connection with the delayed-release microparticles.

Taste-Masking Coating

In some embodiments, the taste masking coating includes a pH-dependent polymer, a plasticizer, and an anti-caking agent.

Examples of pH-dependent polymers are disclosed hereinabove in connection with the immediate release microparticles. An exemplary example for purposes of the taste-masking coating is Eudragit® EPO. The polymer may be present in the taste-masking coating in an amount that ranges from about 0.03 g/g (or 3% w/w) to about 0.6 g/g (or 60% w/w), and in other embodiments, from about 0.1 g/g (or 10% w/w) to about 0.4 g/g (or 40% w/w), based on the coating weight gain on dried basis.

Here too, it is believed that the plasticizer increases the elasticity of the polymer in the taste masking coating, which therefore makes the taste masking coating highly plasticized and substantially crush-resistant. Examples of plasticizers that may be useful in the taste-masking coating composition are provided hereinabove in connection with the IR microparticles and the various coatings that may be applied thereto. In general, the plasticizer may be present in the taste masking coating in an amount that ranges from about 0.02 g/g (or 2% w/w) to about 0.3 g/g (or 30% w/w), and in some embodiments, from about 0.05 g/g (or 5% w/w) to about 0.15 g/g (or 15% w/w), based on the weight of the polymer in the taste-masking coating composition.

Representative examples of anti-caking agents include talc and colloidal silicon dioxide.

Manufacture of Taste-Masked Microparticles

In some embodiments, the taste masking coating composition is prepared by dispersing the plasticizer in purified water, followed by dispersing the anti-caking agent, plasticizer, and the pH-dependent polymer in the solution to form a dispersion, wherein the dispersion is mixed until a uniform dispersion is obtained.

The taste masking coating may be applied to any one or more of the populations of microparticles that are to be present in the final oral dosage composition.

Optional Ingredients

The oral pharmaceutical compositions of the present invention may further include additional, i.e., optional, pharmaceutically inert ingredients, generally known as excipients. Generally, these ingredients may be included in the composition in various ways. In some embodiments, they may be present as extra granular components.

The compositions may include a disintegrant. These ingredients hydrate the composition and aid in table dispersion. Useful disintegrants include carmellose calcium, carboxymethyl starch sodium, croscarmellose sodium, crospovidone (crosslinked homopolymer of N vinyl-2-pyrrolidone), and low substituted hydroxypropyl celluloses. Other useful disintegrants include sodium starch glycolate, colloidal silicon dioxide, alginic acid and alginates, acrylic acid derivatives, and various starches.

The compositions may include a glidant which improves the flow of powder blends, pellets, etc. and minimizes dosage form weight variations. Useful glidants include fumed or colloidal silica, talc, kaolin, or a combination of two or more thereof. Different grades of fumed silica are commercially available from various sources, including the CAB O SIL® products sold by Cabot Corporation and the AEROSIL® products sold by Evonik Industries.

The compositions may include a diluent or filler. Useful fillers or diluents include starches, lactose, cellulose derivatives, confectioner's sugar and the like. Different grades of lactose include lactose monohydrate, lactose DT (direct tableting), lactose anhydrous, and others. Different starches include maize starch, potato starch, rice starch, wheat starch, pregelatinized starch, and others. Different celluloses that can be used include crystalline celluloses, such as microcrystalline cellulose, and powdered celluloses. Other useful diluents include carmellose, sugar alcohols such as mannitol, sorbitol, and xylitol, calcium carbonate, magnesium carbonate, dibasic calcium phosphate, and tribasic calcium phosphate.

The compositions may include a binder. Binders may provide enhanced cohesion or tensile strength. Useful binders include hydroxypropyl celluloses in various grades, hydroxypropyl methylcelluloses in various grades, polyvinylpyrrolidones in various grades, copovidones, powdered acacia, gelatin, guar gum, carbomers, methylcelluloses, polymethacrylates, and starches.

The compositions may include a lubricant. Lubricants may aid in compression for purposes of tablet-making. Useful lubricants include magnesium stearate, glyceryl monostearates, palmitic acid, talc, carnauba wax, calcium stearate sodium, sodium or magnesium lauryl sulfate, calcium soaps, zinc stearate, polyoxyethylene monostearates, calcium silicate, silicon dioxide, hydrogenated vegetable oils and fats, and stearic acid.

The compositions may include a sweetener. Useful sweeteners include sucrose, sucralose, and aspartame.

The compositions may include a flavoring agent. Useful flavoring agents include pharmaceutically acceptable natural oils, natural flavors, and artificial flavors. Representative flavors include menthol, peppermint, wintergreen, orange, cherry, and other fruits, vanilla, almond and other nuts, etc. Mixtures of two or more flavoring agents may be advantageous.

The compositions may include a coloring agent. Coloring agents can be used to color code compositions, for example, to indicate the type and dosage of the therapeutic agent therein. Coloring agents can also be used to differentiate the varied fractions of multi particulates contained in a unit dosage form such as a capsule. Suitable coloring agents include natural and/or artificial colorants such as FD&C coloring agents, natural juice concentrates, pigments such as titanium dioxide, silicon dioxide, iron oxides, zinc oxide, and the like.

The compositions may include a solvent. Representative examples of solvents that may be useful include water, methanol, ethanol, acetone, diacetone, polyols, polyethers, oils, esters, alkyl ketones, methylene chloride, isopropyl alcohol, butyl alcohol, methyl acetate, ethyl acetate, isopropyl acetate, castor oil, ethylene glycol monoethyl ether, diethylene glycol monobutyl ether, diethylene glycol monoethyl ether, dimethylsulfoxide, N,N dimethylformamide, tetrahydrofuran, and mixtures of two or more thereof.

Compositions of the present application may contain an antioxidant. These ingredients may enhance the stability of a drug, particularly during storage. Antioxidants can be present in amounts effective to retard decomposition of a drug that is susceptible to oxidation. The content of an antioxidant in the formulations generally ranges from about 0.001 to 10 weight %, with respect to the amount of the drug. Representative examples of antioxidants include ascorbic acid and its salts, tocopherols, sulfite salts such as sodium metabisulfite or sodium sulfite, sodium sulfide, butylated hydroxyanisole, butylated hydroxytoluene, ascorbyl palmitate, and propyl gallate.

Manufacture of Modified-Release Microparticle Formulation

In some embodiments, the pharmaceutical composition contains one or two or more of the populations of microparticles including the immediate release (IR) microparticles, extended release (ER) microparticles, delayed release (DR) microparticles, and the delayed extended release (DER) microparticles, which may be blended with one or more additives and compressed into an orally disintegrating dosage form such as tablet, or formulated in a capsule (e.g., a hard or soft gelatin capsule). In some embodiments, the microparticles are taste masked. In embodiments that contain more than one population of microparticles, the process steps for making the IR microparticles may be repeated to prepare each population or the original population can be made large enough to subdivide it into subpopulations that can be further treated with the desired release and/or taste-masking coating compositions. The release profile of the pharmaceutical composition is customizable, based on the selected combinations of the immediate release (IR), extended release (ER), and/or delayed release (DR) microparticles, and/or delayed extended release (DER) microparticles. Those of skill in the art will be able to vary the amount of any single microparticle population and the type of microparticles to arrive at a desired release profile depending upon the active pharmaceutical ingredient included therein.

In some embodiments, the IR microparticles (which may be taste-masked), along with any extra-granular excipients, make a final dosage form.

In some embodiments, the ER microparticles (which may be taste-masked), along with any extra-granular excipients, make a final dosage form.

In some embodiments, the DR microparticles (which may be taste-masked), along with any extra-granular excipients, make a final dosage form. In some embodiments, the DR-ER microparticles (which may be taste-masked), along with any extra-granular excipients, make a final dosage form.

In some embodiments, the IR microparticles are blended with ER microparticles and mixed with extra-granular excipients to make a final dosage form. In some embodiments, IR microparticles and/or DR microparticles are coated with a taste masking coating prior to mixing with extra-granular excipients.

In some embodiments, IR microparticles are blended with DR microparticles and mixed with extra-granular excipients to make a final dosage form. In some embodiments, IR microparticles and/or DR microparticles are coated with a taste masking coating prior to mixing with extra-granular excipients.

In some embodiments, IR microparticles are blended with DER microparticles and mixed with extra-granular excipients to make a final dosage form. In some embodiments, IR microparticles and/or DR microparticles are coated with a taste masking coating prior to mixing with extra-granular excipients.

In some embodiments, ER microparticles are blended with DR microparticles and mixed with extra-granular excipients to make a final dosage form. In some embodiments, CR microparticles and/or DR microparticles are coated with a taste masking coating prior to mixing with extra-granular excipients.

In some embodiments, IR microparticles are blended with ER microparticles and DR microparticles and mixed with extra-granular excipients to make a final dosage form. In some embodiments, IR microparticles, ER microparticles and/or DR microparticles are coated with a taste masking coating prior to mixing with extra-granular excipients.

In some embodiments, IR microparticles are blended with ER microparticles and DER microparticles and mixed with extra-granular excipients to make a final dosage form. In some embodiments, IR microparticles, ER microparticles and/or DER microparticles are coated with a taste masking coating prior to mixing with extra-granular excipients.

The following examples further describe certain specific aspects and embodiments of the disclosure, but should not be construed as limiting the scope of the disclosure in any manner.

Example 1

Formulations are prepared, using the ingredients listed in Table 3 below.

TABLE 3

| Ingredients | % w/w |
|---|---|
| Immediate-Release Substantially Crush-Resistant Microparticles | |
| Micronized Ritonovir (active pharmaceutical ingredient) | 56.00 |
| Eudragit ® EPO (polymer matrix) | 40.00 |
| Triethyl citrate (plasticizer) | 4.00 |

Manufacturing Procedure:
Preparation of the substantially crush-resistant microparticle:
1. Blend micronized ritonavir, Eudragit® EPO, and triethyl citrate in a high shear mixer.
2. Pass the blend through a hot melt extruder.
3. Cryomilling the extrudate to achieve a particle size distribution of 25 to 500 Micrometers and mean particle size of 50 to 250 micrometers Example 2

Formulations are prepared, using the ingredients listed in Table 4 below.

TABLE 4

| Ingredients | % w/w |
|---|---|
| Immediate-Release Substantially Crush-Resistant Microparticles | |
| Methylphenidate Hydrochloride (active pharmaceutical ingredient) | 66.00 |
| Hypromellose Acetate Succinate-MF (HPMCAS-MF) (polymer matrix) | 30.00 |
| Triethyl citrate (plasticizer) | 4.00 |

Manufacturing Procedure:
Preparation of the substantially crush-resistant microparticle:
1. Blend methylphenidate hydrochloride, hypromellose acetate succinate-MF, and triethyl citrate in a high shear mixer.
2. Pass the blend through a hot melt extruder.
3. Cryomilling the extrudate to achieve a particle size distribution of 25 to 500 Micrometers and mean particle size of 50 to 250 micrometers Example 3

Formulations are prepared, using the ingredients listed in Table 5 below.

TABLE 5

| Ingredients | mg/tablet |
|---|---|
| Substantially Crush-Resistant Microparticles | |
| Micronized Ritonavir (active pharmaceutical ingredient) | 100.00 |
| Eudragit ® EPO (polymer matrix) | 100.00 |
| Triethyl citrate (plasticizer) | 10.00 |

TABLE 5-continued

| Ingredients | mg/tablet |
|---|---|
| Taste Masking Coat | |
| Eudragit ® EPO | 15.50 |
| Dibutyl sebacate | 1.55 |
| Sodium Lauryl Sulphate | 0.50 |
| Talc | 13.95 |
| External Blend | |
| Mannitol | 20.25 |
| Microcrystalline Cellulose | 20.25 |
| Polyplasdone XL | 15.00 |
| Magnesium Stearate (lubricant) | 3.00 |
| Total Tablet Weight | 300.00 |

Manufacturing Procedure:

1. Preparation of the substantially crush-resistant microparticle:
   a. Blend micronized ritonavir, Eudragit® EPO, and triethyl citrate in a high shear mixer.
   b. Pass the blend through a hot melt extruder.
   c. Cryomilling the extrudate to achieve a particle size distribution of 20 to 500 Micrometers and mean particle size of 50 to 250 micrometers
2. Preparation of Taste Masking Coated Microparticles
   a. Prepare taste masking coating suspension by dissolving sodium lauryl sulphate in purified water, followed by dispersing talc, dibutyl sebacate and Eudragit® EPO.
   b. Mix the dispersion well until a uniform dispersion is obtained.
   c. Coat the substantially crush-resistant microparticles from step 1.c. with taste masking suspension using a Wurster fluid bed coater.
3. Preparation of Orally Disintegrating Tablets
   a. Blend the taste masking coated microparticles with mannitol, microcrystalline cellulose, and polyplasdone XL for 10 minutes in a V-blender. Blend with magnesium stearate for an additional 3 minute.
   b. Compress the blend from step 3.a. into tablets.

Example 4

Formulations are prepared, using the ingredients listed in Table 6 below.

TABLE 6

| Ingredients | mg/tablet |
|---|---|
| Substantially Crush-Resistant Microparticles | |
| Methylphenidate Hydrochloride (active pharmaceutical ingredient) | 40.00 |
| Eudragit ® EPO (polymer matrix) | 40.00 |
| Triethyl citrate (plasticizer) | 4.00 |
| Extended Release Coat | |
| Ethocel 10 cps | 13.6 |
| Triethyl citrate (plasticizer) | 1.4 |
| External Blend | |
| Mannitol | 10.00 |
| Microcrystalline Cellulose | 5.00 |

TABLE 6-continued

| Ingredients | mg/tablet |
|---|---|
| Polyplasdone XL | 10.00 |
| Magnesium Stearate (lubricant) | 1.00 |
| Total Tablet Weight (mg) | 125.00 |

Manufacturing Procedure:

1. Preparation of the substantially crush-resistant microparticle:
   a. Blend micronized methylphenidate hydrochloride, Eudragit® EPO, and triethyl citrate in a high shear mixer.
   b. Pass the blend through a hot melt extruder.
   c. Cryomilling the extrudate to achieve a particle size distribution of 25 to 500 Micrometers and mean particle size of 50 to 250 micrometers
2. Preparation of Extended-Released Coated Microparticles
   a. Prepare functional coating solution by dissolving triethyl citrate and Ethocel in an alcoholic solvent (water:ethanol=20:80).
   b. Coat the substantially crush-resistant microparticles from step 1.c. with functional coating solution in step 2.a. using a Wurster fluid bed coater.
3. Preparation of Orally Disintegrating Tablets
   a. Blend the coated microparticles with mannitol, microcrystalline cellulose, and polyplasdone XL in a V-blender. Blend with magnesium stearate.
   b. Compress the blend from step 3.a. into tablets.

Example 5

Formulations are prepared, using the ingredients listed in Table 7 below.

TABLE 7

| Ingredients | mg/tablet |
|---|---|
| Substantially Crush-Resistant Microparticles | |
| Methylphenidate Hydrochloride (active pharmaceutical ingredient) | 40.00 |
| Hypromellose Acetate Succinate-MF (HPMCAS-MF) (polymer matrix) | 40.00 |
| Triethyl citrate (plasticizer) | 6.00 |
| Delayed Release Coating | |
| Eudragit ® L100 (Poly(methacylic acid-co-methyl methacrylate) 1:1) | 7.0 |
| Eudragit ® S100 (Poly(methacylic acid-co-methyl methacrylate) 1:2) | 7.0 |
| Triethyl Citrate (plasticizer) | 2.8 |

Manufacturing Procedure:

1. Preparation of the substantially crush-resistant microparticle:
   a. Blend micronized methylphenidate hydrochloride, Hypromellose Acetate Succinate, and triethyl citrate in a high shear mixer.
   b. Pass the blend through a hot melt extruder.
   c. Cryomilling the extrudate to achieve a particle size distribution of 25 to 500 Micrometers and mean particle size of 50 to 250 micrometers 2. Preparation of Delayed-Released Coated Microparticles
   a. Prepare delayed release coating solution by dissolving triethyl citrate, Eudragit® L100, and Eudragit® S100 in an alcoholic solvent (water:ethanol=20:80).
   b. Coat the substantially crush-resistant microparticles from step 1.c. with functional coating solution in step 2.a. using a Wurster fluid bed coater.

Example 6

Formulations are prepared, using the ingredients listed in Table 8 below.

TABLE 8

| Ingredients | mg/tablet |
| --- | --- |
| Substantially Crush-Resistant Microparticles | |
| Methylphenidate Hydrochloride (active pharmaceutical ingredient) | 40.00 |
| Eudragit ® EPO (polymer matrix) | 40.00 |
| Triethyl citrate (plasticizer) | 4.00 |
| Extended Release Coating | |
| Ethocel 10 cps | 9.0 |
| Triethyl citrate (plasticizer) | 0.9 |
| Delayed Release Coating | |
| Eudragit ® L100 | 5.0 |
| Eudragit ® S100 | 20.0 |
| Triethyl Citrate (plasticizer) | 5.0 |
| Talcum | 5.0 |

Manufacturing Procedure:
1. Preparation of the substantially crush-resistant microparticle:
   b. Blend micronized methylphenidate hydrochloride, Eudragit® EPO, and triethyl citrate in a high shear mixer.
   c. Pass the blend through a hot melt extruder.
   d. Cryomilling the extrudate to achieve a particle size distribution of 25 to 500 Micrometers and mean particle size of 50 to 250 micrometers
2. Preparation of Extended Release Coated Microparticles
   a. Prepare functional coating solution by dissolving triethyl citrate and Ethocel in an alcoholic solvent (water:ethanol=20:80).
   b. Coat the substantially crush-resistant microparticles from step 1.d. with extended release coating solution in step 2.a. using a Wurster fluid bed coater.
3. Preparation of Delayed Extended Release Coated Microparticles
   a. Prepare delayed coating solution by dissolving triethyl citrate, Eudragit® L100, and Eudragit® S100 in an alcoholic solvent (water:ethanol=20:80).
   b. Disperse talcum in the delayed release coating in step 3.a.
   c. Coat the substantially extended release microparticles from step 2.b. with delayed release coating dispersion in step 3.b. using a Wurster fluid bed coater.

Example 7

Formulations are prepared, using the ingredients listed in Table 9 below.

TABLE 9

| Ingredients | mg/tablet |
| --- | --- |
| Methylphenidate Hydrochloride Immediate Release Microparticles, Type A (Example 2) | 25.00 |
| Methylphenidate Hydrochloride Extended Release Microparticles, Type B (Example 4, Step 2.b.) | 50.00 |
| Methylphenidate Hydrochloride Delayed Release Microparticles, Type C (Example 5) | 27.80 |
| External Blend | |
| Mannitol | 8.10 |
| Microcrystalline Cellulose | 8.10 |
| Polyplasdone XL | 10.00 |
| Magnesium Stearate (lubricant) | 1.00 |
| Total Tablet Weight (mg) | 130.00 |

Manufacturing Procedure:
1. Blend microparticles of Type A, Type B, and Type C with mannitol, microcrystalline cellulose, and polyplasdone XL in V-blender.
2. Lubricate the blend from step 1 with magnesium stearate in v-blender.
3. Compress blend from step 2 into tablets.

Example 8

Formulations are prepared, using the ingredients listed in Table 10 below.

TABLE 10

| Ingredients | mg/tablet |
| --- | --- |
| Methylphenidate Hydrochloride Immediate Release Microparticles, Type A (Example 2) | 25.00 |
| Methylphenidate Hydrochloride Extended Release Microparticles, Type B (Example 4, Step 2.b.) | 50.00 |
| Methylphenidate Hydrochloride Delayed Extended Release Microparticles, Type D (Example 6) | 50.00 |
| External Blend | |
| Mannitol | 8.10 |
| Microcrystalline Cellulose | 15.90 |
| Polyplasdone XL | 10.00 |
| Magnesium Stearate (lubricant) | 1.00 |
| Total Tablet Weight (mg) | 160.00 |

Manufacturing Procedure:
1. Blend microparticles of Type A, Type B, and Type D with mannitol, microcrystalline cellulose, and polyplasdone XL in V-blender.
2. Lubricate the blend from step 1 with magnesium stearate in v-blender.
3. Compress blend from step 2 into tablets.

Example 9

Formulations are prepared, using the ingredients listed in Table 11 below.

TABLE 11

| Ingredients | % w/w | | | |
| --- | --- | --- | --- | --- |
| Immediate-Release Substantially Crush-Resistant Microparticles | | | | |
| Oseltamivir phosphate | 50.00 | 40.00 | 50.00 | 40.00 |
| Eudragit ® EPO (polymer matrix) | 40.00 | 48.00 | 40.00 | 48.00 |

TABLE 11-continued

| Ingredients | % w/w | | | |
|---|---|---|---|---|
| Immediate-Release Substantially Crush-Resistant Microparticles | | | | |
| Dibutyl sebacate (plasticizer) | 10.00 | 12.00 | — | — |
| Stearic Acid (Plasticizer) | — | — | 10.00 | 12.00 |

Manufacturing Procedure:
Preparation of the substantially crush-resistant microparticle.
1. Blend micronized Oseltamivir phosphate, Eudragit® EPO, and dibutyl sebacate or stearic acid in a high shear mixer.
2. Pass the blend through a hot melt extruder.
3. Cryomilling the extrudate to achieve a particle size distribution of 25 to 500 micrometers and mean particle size of 50 to 250 microns.

Example 10

Formulations are prepared, using the ingredients listed in Table 12 below.

TABLE 12

| Ingredients | % w/w | | | |
|---|---|---|---|---|
| Extended-Release Substantially Crush-Resistant Microparticles | | | | |
| Oseltamivir phosphate | 50.00 | 40.00 | 50.00 | 40.00 |
| Hypromellose Acetate Succinate-MF (HPMCAS-MF) (polymer matrix) | 40.00 | 48.00 | 40.00 | 48.00 |
| Dibutyl sebacate (plasticizer) | 10.00 | 12.00 | — | — |
| Glyceryl monostearate (plasticizer) | — | — | 10.00 | 12.00 |

Manufacturing Procedure:
Preparation of the substantially crush-resistant microparticle:
1. Blend Oseltamivir phosphate, hypromellose acetate succinate-MF, and dibutyl sebacate or glyceryl monostearate in a high shear mixer.
2. Pass the blend through a hot melt extruder.
3. Cryomilling the extrudate to achieve a particle size distribution of 25 to 500 Micrometers and mean particle size of 50 to 250 micrometers

Example 11

Formulations are prepared, using the ingredients listed in Table 13 below.

TABLE 13

| Ingredients | mg/tablet |
|---|---|
| Substantially Crush-Resistant Microparticles | |
| Oseltamivir phosphate (active pharmaceutical ingredient) | 45.00 |
| Eudragit ® EPO (polymer matrix) | 36.00 |
| Dibutyl sebacate (plasticizer) | 3.60 |
| External Blend | |
| Xylitol | 52.40 |
| Mannitol 200SD/Pharmaburst 500 | 131.00 |
| Croscarmellose sodium | 18.00 |
| Flavor | 50.00 |

TABLE 13-continued

| Ingredients | mg/tablet |
|---|---|
| Anhydrous citiric acid | 2.00 |
| Sucralose | 9.00 |
| Cab-O-Sil | 1.00 |
| Magnesium stearate (lubricant) | 2.00 |
| Total Tablet Weight | 350.00 |

Manufacturing Procedure:
1. Preparation of the substantially crush-resistant microparticle:
    a. Blend micronized Oseltamivir phosphate, Eudragit® EPO, and dibutyl sebacate in a high shear mixer.
    b. Pass the blend through a hot melt extruder.
    c. Cryomilling the extrudate to achieve a particle size distribution of 25 to 500 Micrometers and mean particle size of 50 to 250 micrometers
2. Preparation of Orally Disintegrating Tablets
    a. Blend the milled microparticles with xylitol, mannitol, croscarmellose sodium, anhydrous citric acid, sucralose and Cab-0-Sil for 10 minutes in a V-blender. Blend with magnesium stearate for an additional 3 minute.
    b. Compress the blend from step 2.a. into tablets.

Example 12

Formulations are prepared, using the ingredients listed in Table 14 below.

TABLE 14

| Ingredients | mg/tablet |
|---|---|
| Substantially Crush-Resistant Microparticles | |
| Oseltamivir phosphate (active pharmaceutical ingredient) | 75.00 |
| Hypromellose Acetate Succinate-MF (HPMCAS-MF) (polymer matrix) | 90.00 |
| Dibutyl sebacate (plasticizer) | 9.00 |
| External Blend | |
| Mannitol | 132.00 |
| Microcrystalline Cellulose | 90.00 |
| Magnesium Stearate (lubricant) | 4.00 |
| Total Tablet Weight | 400.00 |

Manufacturing Procedure:
1. Preparation of the substantially crush-resistant microparticle:
    a. Blend micronized Oseltamivir phosphate, hypromellose acetate succinate-MF, and dibutyl sebacate in a high shear mixer.
    b. Pass the blend through a hot melt extruder.
    c. Cryomilling the extrudate to achieve a particle size distribution of 25 to 500 Micrometers and mean particle size of 50 to 250 micrometers
2. Preparation of Extended Release Tablets
    a. Blend the milled microparticles with mannitol, microcrystalline cellulose for 10 minutes in a V-blender. Blend with magnesium stearate for an additional 3 minute.
    b. Compress the blend from step 2.a. into tablets.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for making an oral pharmaceutical composition, comprising a) making crush resistant immediate-release (IR) microparticles; b) optionally coating the crush resistant IR microparticles; and c) formulating the optionally coated crush resistant IR microparticles into an oral pharmaceutical composition;

wherein the step of making crush resistant IR microparticles comprises:
1) subjecting a therapeutically effective amount of an active pharmaceutical ingredient, a cationic pH-dependent polymer, and a plasticizer, each in amounts effective to render the IR microparticles crush resistant, to hot melt extrusion to obtain extrudates, and
2) milling the extrudates using downstream processing equipment to produce a population of crush resistant IR microparticles with a mean particle size ranging from about 50 microns to about 250 microns.

2. The method of claim 1, wherein the oral pharmaceutical composition is an orally disintegrating tablet.

3. The method of claim 1, further comprising coating the crush resistant IR microparticles with an extended release (ER) coating composition, prior to step c), thus the oral pharmaceutical composition comprises a population of ER microparticles.

4. The method of claim 3, wherein the ER coating composition comprises a plasticizer, and a nonionic pH-independent polymer.

5. The method of claim 1, further comprising coating the crush resistant IR microparticles with a delayed release (DR) coating composition, prior to step c), thus the oral pharmaceutical composition comprises a population of DR microparticles.

6. The method of claim 5, wherein the DR coating composition comprises a plasticizer, and an anionic pH-dependent polymer.

7. The method of claim 1, further comprising coating the crush resistant IR microparticles with an extended release (ER) coating composition and a delayed release (DR) coating composition, prior to step c), thus the oral pharmaceutical composition comprises a population of delayed extended release (DER) microparticles.

8. The method of claim 1, further comprising coating the crush resistant IR microparticles with a taste-masking coating composition, prior to step c), thus the oral pharmaceutical composition comprises a population of taste-masked IR microparticles.

9. The method of claim 3, further comprising coating the ER microparticles with a taste-masking coating composition, prior to step c), thus the oral pharmaceutical composition comprises a population of taste-masked ER microparticles.

10. The method of claim 5, further comprising coating the DR microparticles with a taste-masking coating composition, prior to step c), thus the oral pharmaceutical composition comprises a population of taste-masked DR microparticles.

11. The method of claim 7, further comprising coating the DER microparticles with a taste-masking coating composition, prior to step c), thus the oral pharmaceutical composition comprises a population of taste-masked DER microparticles.

12. The method of claim 1, further comprising: i) subdividing the crush resistant IR microparticles from step 2) into at least two subpopulations of the crush resistant IR microparticles; coating one subpopulation of the crush resistant IR microparticles from step i) with at least one of an extended release (ER) coating composition, a delayed release (DR) coating composition, or an extended release (ER) coating composition and a delayed release (DR) coating composition, to produce at least one population of ER microparticles, DR microparticles, or delayed extended release (DER) microparticles, iii) coating one subpopulation of the crush resistant immediate-release (IR) microparticles from step i), and the at least one population of ER microparticles, DR microparticles, or delayed extended release (DER) microparticles from step ii) with a taste-masking coating composition to produce taste-masked IR microparticles, and at least one population of taste-masked ER microparticles, taste-masked DR microparticles, or taste-masked DER microparticles, and iv) mixing the subpopulation of the crush resistant immediate-release (IR) microparticles if present from step i), and the at least one population of taste-masked IR microparticles, taste-masked ER microparticles, taste-masked DR microparticles, or taste-masked DER microparticles from step iii, prior to step c).

13. The method of claim 1, wherein the active pharmaceutical ingredient is methylphenidate.

14. The method of claim 1, wherein the plasticizer is selected from the group consisting of dibutyl sebacate and triethyl citrate.

15. The method of claim 1, wherein the cationic pH-dependent polymer comprises a copolymer of butyl methacrylate, (2-dimethylaminoethyl) methacrylate, and methyl methacrylate.

16. The method of claim 4, wherein the nonionic pH-independent polymer is selected from the group consisting of polyvinyl acetate/polyvinylpyrrolidone, cellulose acetate, cellulose acetate butyrate, ethyl cellulose, copolymer of ethyl acrylate, methyl methacrylate, and a low content of methacrylic acid ester with quaternary ammonium groups 1:2:0.1 (EUDRAGIT® RS 100), and copolymer of ethyl acrylate, methyl methacrylate, and a low content of methacrylic acid ester with quaternary ammonium groups 1:2:0.2 (EUDRAGIT® RL 100).

17. The method of claim 6, wherein the anionic polymer is selected from the group consisting of a copolymer of methacrylic acid and methyl methacrylate 1:1 (EUDRAGIT® L100), a copolymer of methacrylic acid and methyl methacrylate 1:2 (EUDRAGIT® S100), hydroxypropyl methylcellulose phthalate, hypromellose acetate succinate, cellulose acetate phthalate, and polyvinyl acetate phthalate.

* * * * *